United States Patent [19]

Godtfredsen

[11] Patent Number: 5,362,719

[45] Date of Patent: Nov. 8, 1994

[54] USE OF VITAMIN-D ANALOGUES IN THE TREATMENT OF ACNE

[75] Inventor: Wagn Ole Godtfredsen, Varlose, Denmark

[73] Assignee: Leo Pharmaceutical Products, Ltd. a/s Lovens Kemiske Fabrik Produktionsaktieselskab), Ballerup, Denmark

[21] Appl. No.: 156,630

[22] Filed: Nov. 24, 1993

Related U.S. Application Data

[63] Continuation-in-part of Ser. No. 859,529, Jun. 11, 1992, Pat. No. 5,292,727.

[30] Foreign Application Priority Data

Mar. 1, 1990 [GB] United Kingdom ............... 9004544

[51] Int. Cl.⁵ .............................................. A61K 31/59

[52] U.S. Cl. .................................... 514/167; 552/653; 514/859; 514/168

[58] Field of Search ................. 514/167, 168; 552/653

[56] References Cited

U.S. PATENT DOCUMENTS

| | | | |
|---|---|---|---|
| 5,104,864 | 4/1982 | DeLuca | 514/167 |
| 5,145,846 | 9/1992 | Baggiolini et al. | 514/167 |
| 5,292,727 | 3/1994 | Godtfredsen | 514/167 |

*Primary Examiner*—Marianne M. Cintins
*Assistant Examiner*—T. J. Criares
*Attorney, Agent, or Firm*—Cushman, Darby & Cushman

[57] ABSTRACT

The invention relates to the use of certain vitamin D analogues for the treatment of acne. The analogues have only moderate activity on the calcium metabolism when compared to 1,25-$(OH)_2D_3$, but retain the ability to activate receptors for 1,25-$(OH)_2D_3$ not associated with calcium absorption or bone calcium mobilization.

2 Claims, No Drawings

USE OF VITAMIN-D ANALOGUES IN THE TREATMENT OF ACNE

This application is a continuation-in-part of Ser. No. 07/859,529, filed Jun. 11, 1992, now U.S. Pat. No. 5,292,727 the contents of which are incorporated herein by reference.

This invention relates to the use of certain Vitamin D analogues in the treatment of acne.

Among the factors contributing to the aetiology of acne, an increased sebum production appears to be of major importance, as the severity of the acne parallels sebum excretion rates.

In accordance with this, the reduction of sebum production induced by treatment with oestrogens or isotretinoin leads to an improvement in acne. However, the hormonal effects of the former precludes its widespread use, and isotretinoin is teratogenic and is only used for very severe acne due to this and other side effects (*Drug and Therapeutics Bulletin*, Vol. 22, No. 24, Dec. 3, 1984).

Recently it has been found that topical application of 1α,25-dihydroxyvitamin $D_3$ (1α, 25-$(OH)_2D_3$) reduces the size of sebaceous glands in the ear of male Syrian hamsters (V. L. Malloy et al, The tricontinental Meeting for Investigative Dermatology, Washington, USA, 1989).

However, this observation may be of limited utility in the human medicine because transdermal absorption after topical application of 1α,25-$(OH)_2D_3$ or systemic treatment with this compound, may, due to its potent calcemic activity, give rise to undesired effects leading to hypercalcemia.

The present invention is based on the finding that vitamin D analogues which have only moderate activity on calcium metabolism compared to 1,25-$(OH)_2D_3$, but which retain the ability to activate receptors for 1,25-$(OH)_2D_3$ not associated with calcium absorption or bone calcium mobilization make it possible to treat acne successfully without having the risk of inducing hypercalcemia.

Examples of such vitamin D analogues for such use are given in the above-mentioned Ser. No. 07/859,529. Particularly preferred for the treatment of acne are (1) calcipotriol (which is also designated herein as MC 903), a compound disclosed in Example 5 of international patent application No. PCT/DK86/0081, international filing date of Jul. 14, 1986, International Publication No. WO 87/00834; see also Calverley, J., *Tetrahedron*, 43:4609–4619 (1987); Binderup, L. and Bramm, E., *Biochemical Pharmacology*, 37:889–895 (1988)) and (2) the compound designated for convenience as KH 1060 which is disclosed in international patent application No. PCT/DK 90/00036 (Example 5, compound No. 106) i.e. 1(S),3(R)-dihydroxy-20(R)-(4'-hydroxy-4'-ethyl-1'-hexyloxy)-9,10-seco-pregna-5(Z),7(E),10(19)-triene. See also U.S. application Ser. No. 08/016,186, filed Feb. 11, 1993 as a continuation of Ser. No. 07/721,562, filed Aug. 2, 1991, the contents of said PCT and U.S. applications being incorporated herein by reference.

The above-mentioned compounds can be used in the form of pharmaceutical preparations, particularly topical formulations, of the type which are generally useful for treating human disorders such as liniments, lotions or creams which in addition to the vitamin D analogue in question may contain further active ingredients. The concentration of the active ingredients will depend upon the choice of vitamin D analogue but will generally be between 1 and 100 µg/g.

The formulations may be applied once or twice daily for prolonged periods of time.

The compositions prepared according to the present invention comprise the active compound in association with a pharmaceutically acceptable carrier therefor and optionally, as noted, other therapeutic ingredient(s). The carrier(s) must be "acceptable" in the sense of being compatible with the other ingredients of the preparations and not deleterious to the recipient thereof.

The compositions may conveniently be prepared by any of the methods well known in the art of pharmacy. Such methods include the step of bringing the active compound into association with the carrier which constitutes one or more accessory ingredients. In general, the preparations are prepared by uniformly and intimately bringing the active compound into association with a liquid carrier or a finely divided solid carrier or both, and then, if necessary, shaping the product into the desired preparation.

Preparations suitable for topical administration include liquid or semi-liquid preparations such as liniments, lotions, oil-in-water or water-in-oil emulsions such as creams, ointments or pastes; or solutions or suspensions such as drops.

In addition to the aforementioned ingredients, the preparations of this invention may include one or more additional ingredients such as diluents, buffers, flavoring agents, binders, surface active agents, thickeners, lubricants, preservatives, e.g. methyl hydroxybenzoate (including anti-oxidants), emulsifying agents and the like.

The preparations may, as mentioned above, contain further therapeutically active compounds usually applied in the above-mentioned treatment.

Preparations suitable for oral administration may be in the form of discrete units such as capsules, sachets, tablets or lozenges, each containing a predetermined amount of the active compound; in the form of a powder or granules; in the form of a solution or a suspension in an aqueous liquid or non-aqueous liquid; or in the form of an oil-in-water emulsion or a water-in-oil emulsion. The active compound may also be administered in the form of a bolus, electuary or paste.

A tablet may be made by compressing or molding the active compound optionally with one or more accessory ingredients. Compressed tablets may be prepared by compressing, in a suitable machine, the active compound in a free-flowing form such as a powder or granules, optionally mixed by a binder, lubricant, inert diluent, surface active or dispersing agent. Molded tablets may be made by molding, in a suitable machine, a mixture of the powdered active compound and suitable carrier moistened with an inert liquid diluent.

Preparations for rectal administration may be in the form of a suppository incorporating the active compound and a carrier such as cocoa butter, or in the form of an enema.

Preparations suitable for parenteral administration conveniently comprise a sterile oily or aqueous preparation of the active compound which is preferably isotonic with the blood of the recipient.

The oral preparations are formulated, preferably as tablets, capsules, or drops, containing from 0.5–1000 µg of the vitamin D analogues or metabolites, per dosage unit.

The present invention particularly concerns a method for treating patients suffering from acne, said method consisting of administering topically to a patient in need of treatment an effective amount of one or more of the above-mentioned vitamin D analogues or metabolites, alone or in combination with one or more other therapeutically active compounds usually applied in such treatment. The treatment with the present compounds concomitantly with further therapeutically active compounds may be simultaneous or with intervals.

The invention will now be further described in the following non-limiting Examples:

Example 1

Cream Containing MC 903 (calcipotriol)

In 1 g almond oil was dissolved 1 mg MC 903. To this solution was added 40 g of mineral oil and 20 g of self-emulsifying beeswax. The mixture was heated to liquify. After the addition of 40 ml hot water, the mixture was mixed well. The resulting cream contains approximately 10 μg of MC 903 per gram of cream.

Example 2

Cream containing 22-oxa-1α,25-dihydroxy vitamin $D_3$

By using the procedure described in Example 1, but replacing MC 903 with 22-oxa-1α,25-dihydroxy vitamin $D_3$, the desired cream was obtained.

EXAMPLE 3

Cream containing 50μg MC 903/g

| MC 903 | | 50 mg |
|---|---|---|
| Cetomacrogol 1000 | | 25 g |
| Cetostearyl alcohol | | 75 g |
| Chloroallylhexaminium chloride | | 0.5 g |
| Glycerol | | 30 g |
| Disodium hydrogenphosphate | | 2 g |
| Sodium dihydrogenphosphate | | 0.1 g |
| Liquid paraffin | | 60 g |
| Polyoxyethylene stearylether | | 12 g |
| White petrolatum | | 160 g |
| Purified water | up to | 1000 g |

Dissolve MC 903 in a solution of glycerol, disodium hydrogenphosphate, sodium dihydrogenphosphate and polyoxyethylene stearylether dissolved in water. Mix with the melted cetomacrogol 1000, liquid paraffin, cetostearyl alcohol and white petrolatum. Homogenize the emulsion and cool. Dissolve chloroallylhexaminium chloride in part of the water and mix until homogeneous with the emulsion. Fill the cream in aluminum tubes.

EXAMPLE 4

Cream containing 100 μg MC 903/g

| MC 903 | | 100 mg |
|---|---|---|
| Cetomacrogol 1000 | | 30 g |
| Cetostearyl alcohol | | 60 g |
| Chloroallylhexaminium chloride | | 0.5 g |
| Propylenglycol | | 30 g |
| Disodium hydrogenphosphate | | 2 g |
| Sodium dihydrogenphosphate | | 0.1 g |
| Liquid paraffin | | 50 g |
| White petrolatum | | 170 g |
| Purified water | up to | 1000 g |

Melt cetomacrogol 1000, cetostearyl alcohol, liquid paraffin and white petrolatum at 75° C. Dissolve propylenglycol in water at 75° C. and mix the solution with the fatty phase. Homogenize the emulsion and cool to 30° C. Mill MC 903 to particle size below 5 μm and suspend in an aqueous solution of disodium hydrogenphosphate, sodium dihydrogenphosphate and chloroallylhexaminium chloride. Add the suspension to the emulsion and fill the cream in tubes.

EXAMPLE 5

Lotion containing 50 μg MC 903/g

| MC 903 | | 50 mg |
|---|---|---|
| Absolute alcohol | | 400 g |
| Hydroxypropylcellulose | | 1 g |
| Menthol | | 1 g |
| Sodium citrate | | 1 g |
| Propylenglycol | | 40 g |
| Purified water | up to | 1000 ml |

Dissolve hydroxypropylcellulose, sodium citrate and propylenglycol in water. Mix with a solution of MC 903 and menthol in absolute alcohol. Fill the lotion in polyethylene plastic bottles.

EXAMPLE 6

Capsules containing 22-oxa-1α,25-dihydroxy vitamin $D_3$ 22-oxa-1α,25-dihydroxy vitamin $D_3$ ('22-oxa') was suspended in arachis oil to a final concentration of 5 μg '22-oxa'/ml oil. 10 Parts by weight of gelatine, 5 parts by weight of glycerine, 0.08 parts by weight potassium sorbate, and 14 parts by weight distilled water were mixed together with heating and formed into soft gelatine capsules. These were then filled each with 100 μl of the '22-oxa' in oil suspension, such that each capsule contained 0.5 μg '22-oxa'.

EXAMPLE 7

Use of MC 903 lotion in the treatment of acne vulgaris of the face

A total of 10 patients with acne vulgaris of the face have been assessed in an open, non-controlled study of MC 903 lotion. Patients were treated for up to 6 weeks with twice daily applications of the lotion: 50 μg/ml. The study provided evidence that MC 903 lotion was well tolerated. Furthermore, the data pertaining to the therapeutic efficacy of the lotion are encouraging.

The compound designated as KH 1060 (compound No. 106, Example 5, U.S. Ser. No. 08/016,186) may also be used in the manner exemplified above as a replacement for, or together with, MC 903.

The advantages of the present invention are further illustrated by studies carried out on rhino mice. Such mice represent a known model for the study of comedolytic potency of drugs used in the treatment of acne (see *Anat. Rec.*, 170:485–500, 1971; *Pharmacology of Retinoids in the Skin*, Reichert U., Shoot B. eds., Karger, Basel, 1989, pps. 144–148; and *Skin Pharmacol.*, 4:65–73, 1991). The skin of such mice has spontaneously a high density of utricles filled with cornified material closely resembling human comedos.

The mice were treated for three consecutive weeks with calcipotriol 50 μg/ml buffered isopropanol solution, all-trans retinoid acid 0.5% cream (A-vitaminsyre ® cream, Nycomed DAK A/S) as a positive control, and buffered isopropanol solution with no active drug serving as control. At the end of the study, skin samples were obtained and prepared for histology, and the number of comedos per centimeter of stratum corneum was counted under a microscope.

Calcipotriol as well as all-trans retinoid acid resulted in a significant reduction (p 0,001, two sample t-test) in comedos in comparison with the placebo treatment. There was no statistically significant difference between the two active treatments.

The study of rhino mice referred to above also included KH 1060 applied as an isopropanol solution 0.5 μg/ml. KH 1060 had a significant comedolytic effect. There was no statistically significant difference between the three active treatments. KH 1060 is a 20-epi analogue of vitamin $D_3$ with potent effect on cell proliferation but a calcaemic effect comparable to calcitriol (*Biochem. Pharmacol.*, 42:1569-79, 1991).

In summary, results on the rhino mouse model demonstrate that both calcipotriol, and KH 1060, have a strong comedolytic action comparable to all-trans retinoid acid. The results obtained with the rhino mouse model demonstrate that calcipotriol, and KH 1060 attack a key point in the development of the acne disease, i.e. the comedo formation.

It is noted that calcipotriol (MC 903) has the formula:

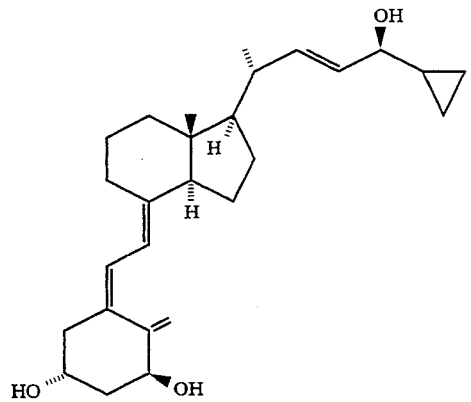

KH 1060 is structurally shown as follows:

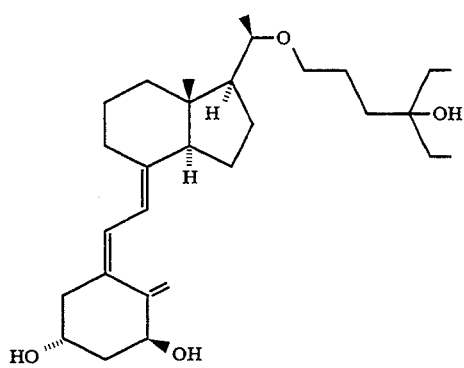

Having described the invention, what we claim as new is:

1. The method of treating acne which comprises administering to a subject in need of such treatment an effective amount of 1(S),3(R)-dihydroxy-20(R)-(4'-hydroxy-4'-ethyl-1'-hexyloxy)-9,10-seco-pregna-5(Z),7(E),10(19)-triene.

2. The method of claim 1 wherein said compound is administered topically.

* * * * *